United States Patent [19]

Haber et al.

[11] Patent Number: 5,372,590
[45] Date of Patent: Dec. 13, 1994

[54] MULTI-CELLED SAFETY PACKAGE, NEEDLE GUARD AND SAFETY DISPOSAL MODULE WITH SLEEVE FOR PREFILLED MEDICATION CARTRIDGES

[75] Inventors: Terry M. Haber, Lake Forest; William H. Smedley, Lake Elsinore; Clark B. Foster, Laguan Niguel, all of Calif.

[73] Assignee: Habley Medical Technology Corporation, Laguna Hills, Calif.

[21] Appl. No.: 105,654

[22] Filed: Aug. 10, 1993

Related U.S. Application Data

[63] Continuation of Ser. No. 596,805, Oct. 12, 1990, abandoned, which is a continuation-in-part of Ser. No. 558,878, Jul. 27, 1990.

[51] Int. Cl.$^5$ .............................................. A61M 5/32
[52] U.S. Cl. .................................. 604/192; 604/110; 604/195; 604/232
[58] Field of Search ............... 604/192, 193, 194, 218, 604/232, 233, 234, 220, 110, 111, 228, 195, 158, 187, 197; 128/919; 206/364–366

[56] References Cited

U.S. PATENT DOCUMENTS

| | | | |
|---|---|---|---|
| 2,880,723 | 4/1959 | Adams | 604/193 |
| 2,888,923 | 6/1959 | Da Cunha Reis | . |
| 2,925,083 | 2/1990 | Craig | . |
| 3,084,688 | 4/1963 | McConnaughey | 604/232 |
| 3,130,724 | 4/1964 | Higgins et al. | 604/234 X |

(List continued on next page.)

FOREIGN PATENT DOCUMENTS

| | | | |
|---|---|---|---|
| 7315527 | 6/1974 | Netherlands | 604/193 |
| 2005505 | 3/1989 | Spain | 128/919 |
| 2227940 | 8/1990 | United Kingdom | 128/919 |

*Primary Examiner*—C. Fred Rosenbaum
*Assistant Examiner*—V. Alexander
*Attorney, Agent, or Firm*—Townsend and Townsend Khourie and Crew

[57] ABSTRACT

A self-packaging safety syringe set (2) uses a unitary molded set of enclosure units (8, 104) sized for housing conventional cartridge-needle units (12) therein. The set of enclosure units are connected to one another by frangible connections (64, 66; 130, 138). The cartridge-needle unit has a hollow barrel (14) with a needle assembly (24) mounted to one end and a piston (16) mounted therein. Each enclosure unit includes a body section (38, 106), a stem section (44, 108) frangibly connected to one end of the body section, and an end cap (52, 110) connected to the other end of the body section. The frangible connection (48, 118) is broken to free the stem section from the body. The removed stem section is used to drive the piston within the barrel. After use, the barrel is pulled back through the body section so that the needle is completely housed within the body section. In one embodiment of the invention, a spring finger (84) engages the hub (34) of the needle assembly to keep the needle assembly from being withdrawn from the body section to permit a safe disposal package for the used syringe. In an alternative embodiment, a plurality of spring fingers are used (132, 134) to secure the needle assembly. In an additional embodiment, a sleeve (15) is frangibly connected to the body portion (38) and can be positioned about the body portion to inwardly bias a detent (174) to engage the hub (34) of the needle assembly to secure it in place. In still a further embodiment, stabilizing tabs (218) are pivotally connected to the body portion (38) and can be positioned in a locked position to centrally position the cartridge needle unit (12) within the body portion (38). The syringe set needs no special packaging and no holders for the cartridge-needle units, the enclosure units serving as both.

13 Claims, 12 Drawing Sheets

U.S. PATENT DOCUMENTS

| | | | |
|---|---|---|---|
| 3,356,089 | 12/1967 | Francis . | |
| 3,366,113 | 1/1968 | Hobbs | 604/111 |
| 3,783,997 | 1/1974 | Brown | 206/43 |
| 3,820,652 | 6/1974 | Thackston | 206/365 |
| 3,916,893 | 11/1975 | De Felice . | |
| 4,334,536 | 6/1982 | Pfleger . | |
| 4,445,895 | 5/1984 | Margulies | 604/193 |
| 4,507,117 | 3/1988 | Vining et al. . | |
| 4,581,023 | 4/1986 | Kuntz | 604/234 |
| 4,592,744 | 6/1986 | Jagger et al. . | |
| 4,710,170 | 12/1987 | Haber et al. | 604/110 |
| 4,790,822 | 12/1988 | Haining . | |
| 4,808,169 | 2/1989 | Haber et al. . | |
| 4,826,489 | 5/1989 | Haber et al. . | |
| 4,834,717 | 5/1989 | Haber et al. | 604/193 |
| 4,846,796 | 7/1989 | Carrell et al. . | |
| 4,888,002 | 12/1989 | Braginetz et al. . | |
| 4,904,242 | 2/1990 | Kulli | 604/110 |
| 4,909,794 | 3/1990 | Haber et al. . | |
| 4,919,652 | 4/1990 | Alter et al. . | |
| 4,932,945 | 6/1990 | Braginetz et al. . | |
| 4,950,241 | 8/1990 | Ranford et al. | 604/110 |
| 4,950,251 | 8/1990 | Haining . | |
| 4,978,340 | 12/1990 | Terril et al. | 604/195 |
| 4,986,813 | 1/1991 | Blake et al. | 604/110 |
| 5,019,043 | 5/1991 | Segui Pastor et al. | 604/110 |
| 5,030,209 | 7/1991 | Wanderer et al. | 604/198 |
| 5,045,066 | 9/1991 | Scheuble et al. | 604/198 |
| 5,066,277 | 11/1991 | Carrell et al. | 604/110 |
| 5,067,947 | 11/1991 | Volk et al. | 604/201 |
| 5,067,948 | 11/1991 | Haber et al. | 604/213 |
| 5,098,402 | 3/1992 | Davis | 604/195 |
| 5,112,307 | 5/1992 | Haber et al. | 604/110 |
| 5,112,315 | 5/1992 | Gloyer et al. | 604/195 |
| 5,112,316 | 5/1992 | Venturini | 604/195 |
| 5,116,319 | 5/1992 | van den Haak | 604/110 |
| 5,232,459 | 8/1993 | Hjertman | 604/208 |

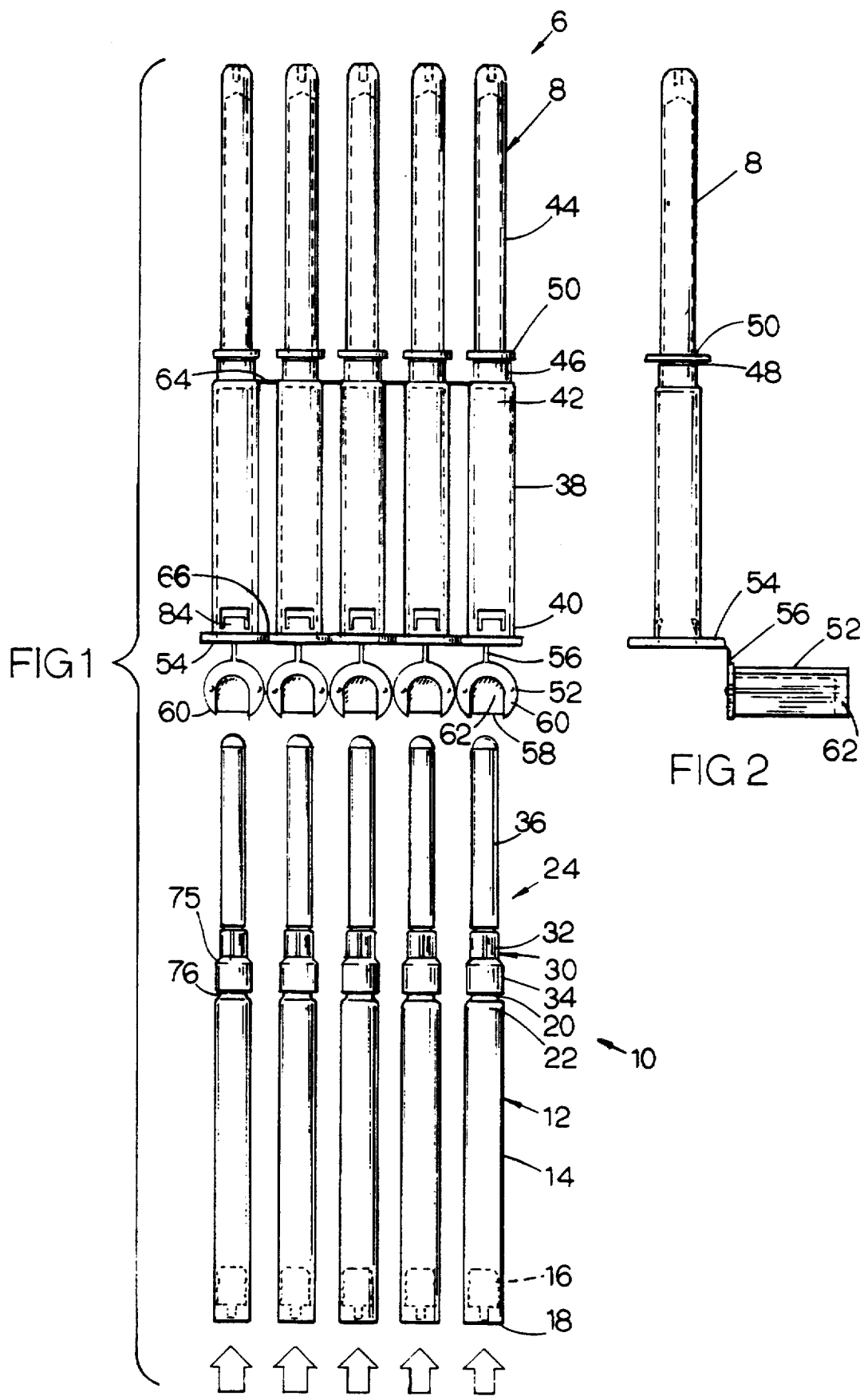

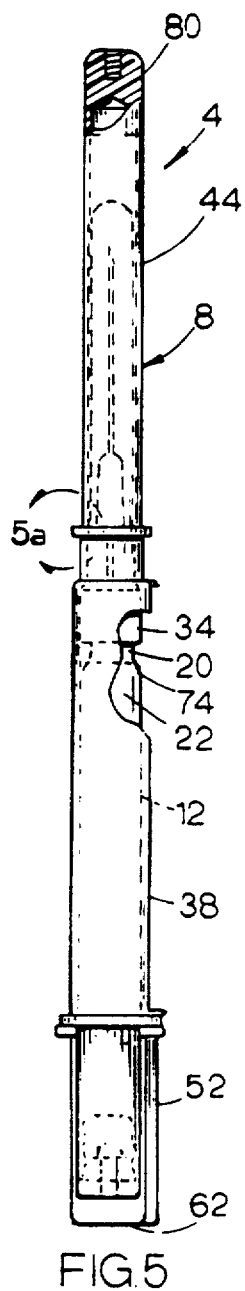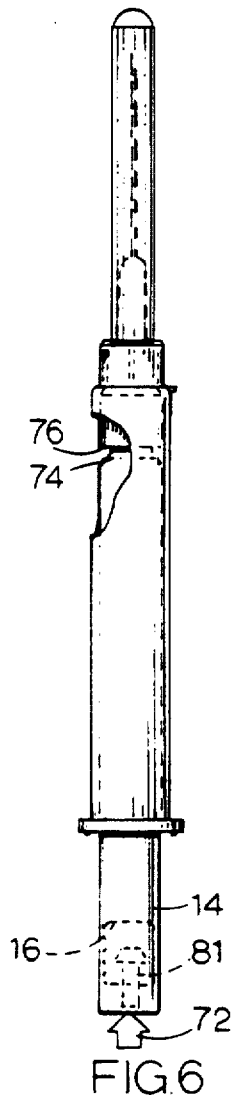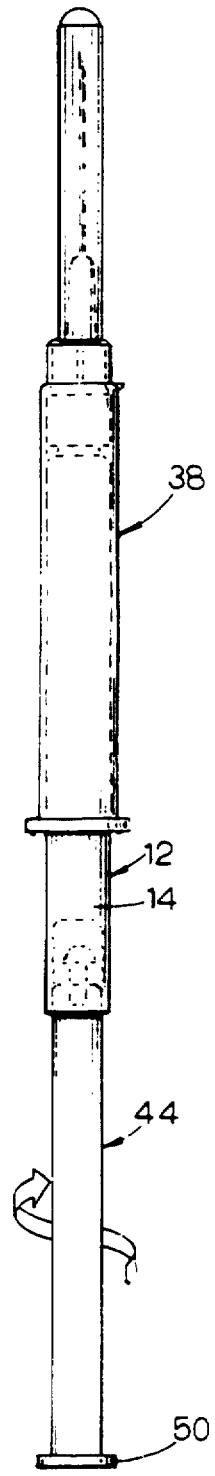
FIG.5
FIG.6
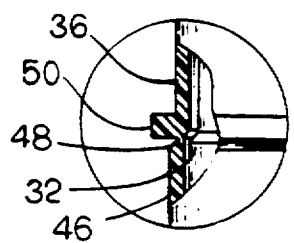
FIG.5a
FIG.7

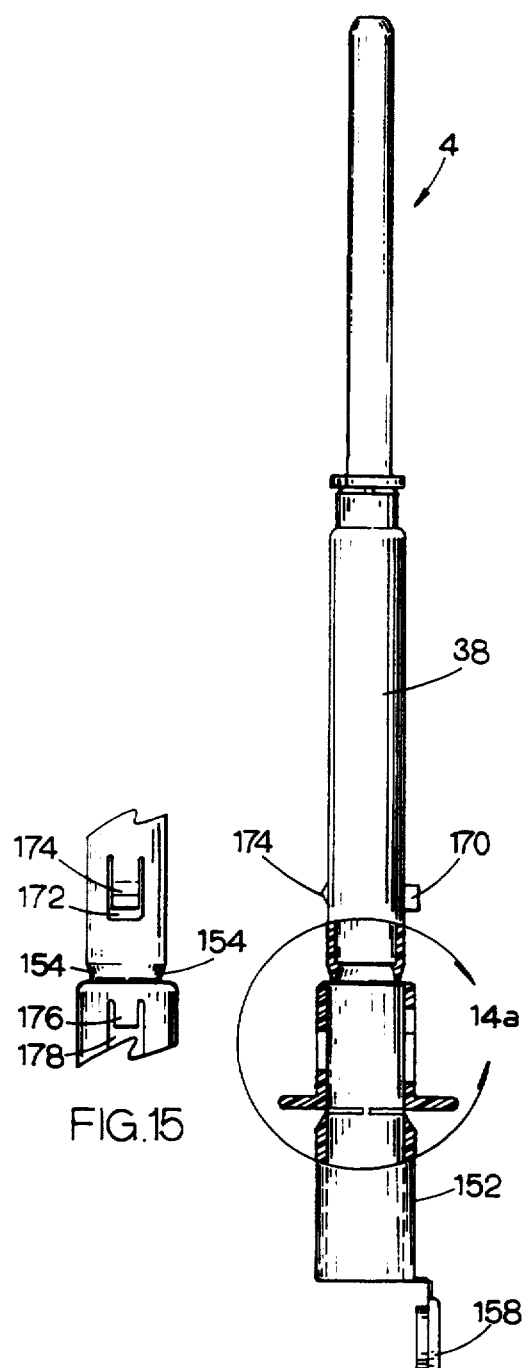
FIG.15
FIG.14
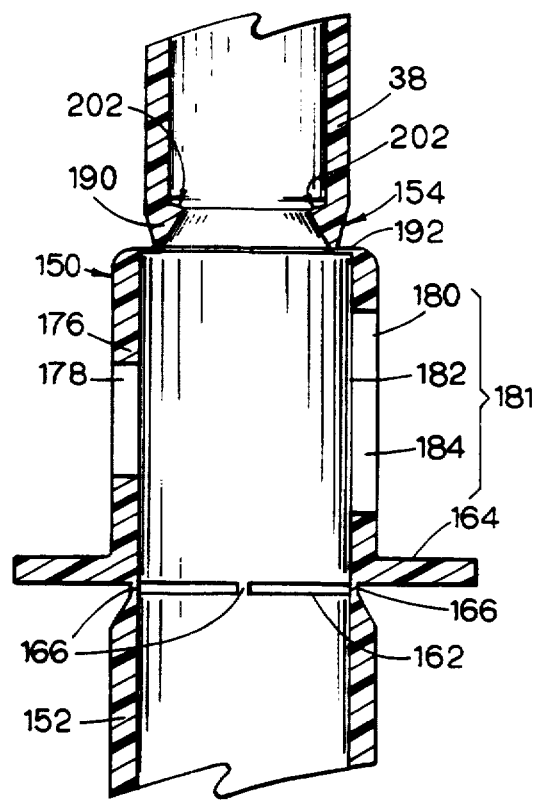
FIG.14a

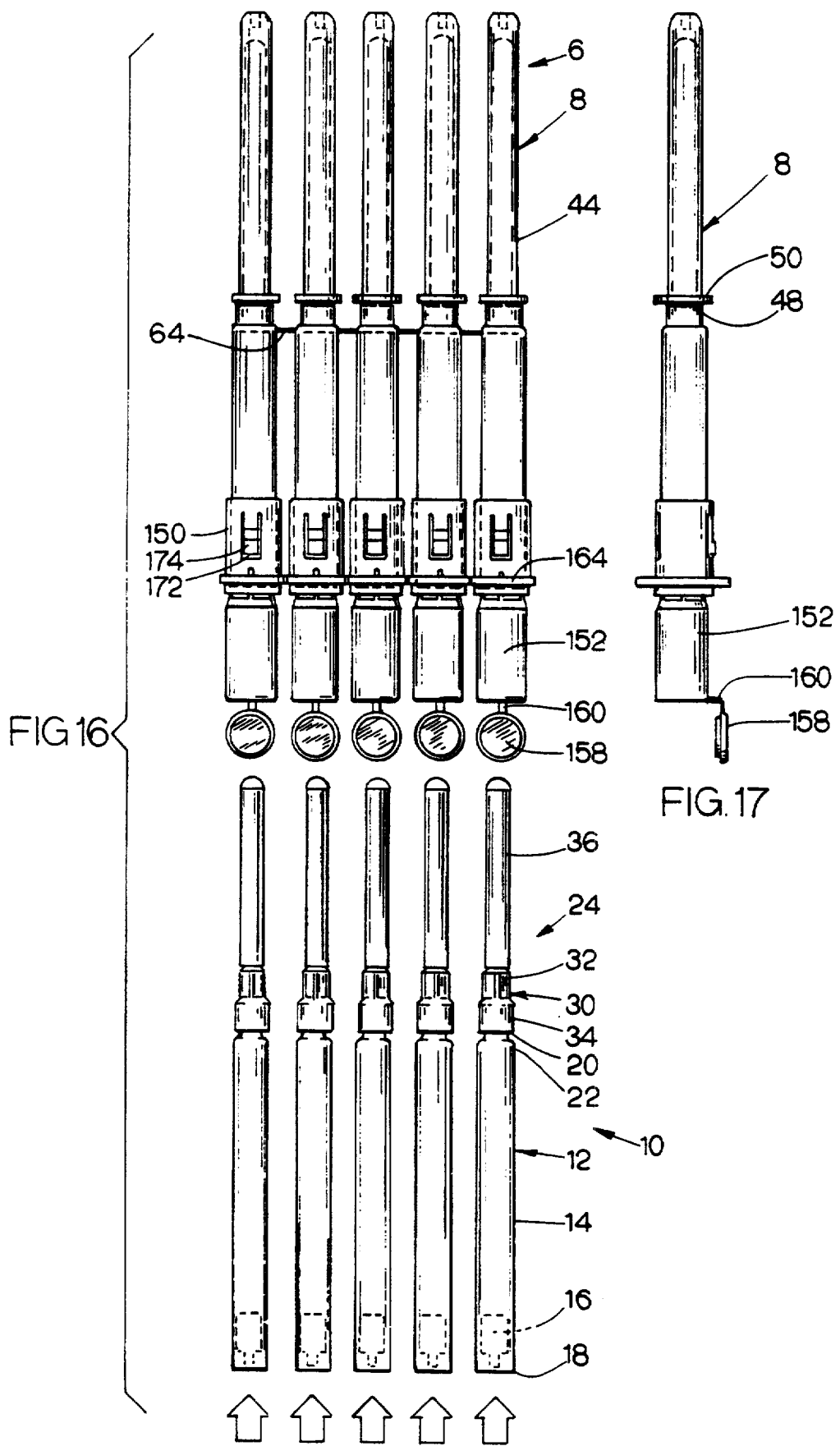

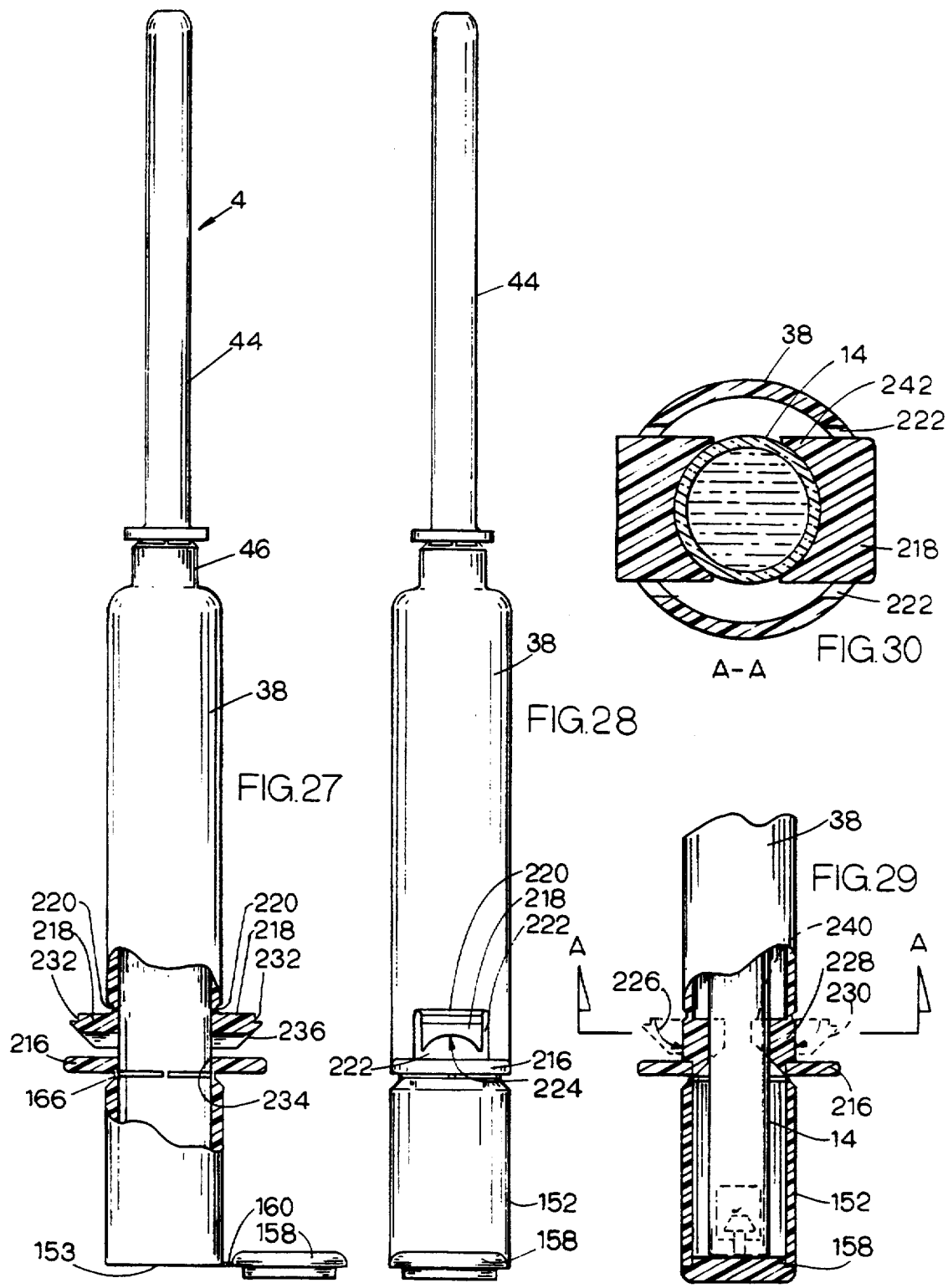

MULTI-CELLED SAFETY PACKAGE, NEEDLE GUARD AND SAFETY DISPOSAL MODULE WITH SLEEVE FOR PREFILLED MEDICATION CARTRIDGES

This is a continuation of application Ser. No. 07/596,805, filed Oct. 12, 1990, now abandoned, which is a continuation-in-part of Applicant's co-pending application Ser. No. 07/558,878 filed Jul. 27, 1990.

BACKGROUND OF THE INVENTION

Many medications are provided in fixed dosage cartridge-needle units. Cartridge-needle units include a glass barrel to which a needle assembly is mounted at one end. The barrel is filled with a medicine. The medicine is held within the barrel by a piston at one end and, typically, a rubber diaphragm at the needle end. The needle assembly is typically mounted to a necked down region of the barrel by a hub. The inner end of the needle is mounted within the hub to a position just opposite the rubber diaphragm. To activate the cartridge-needle unit, the barrel and needle assembly are pushed towards one another so that the inner end of the needle punctures the diaphragm to allow the medicine within the barrel to flow through the needle.

Cartridge-needle units are commonly used with a reusable holder. Holders have a body within which the cartridge-needle unit is placed. The holder includes a stem or plunger which is mounted, typically threaded, to the piston. The sheath covering the needle is removed and the injection is given. After use, the plunger is uncoupled from the piston and the used cartridge-needle unit is removed from the body and disposed of.

While the use of cartridge-needle units has many advantages, there are drawbacks as well. Several cartridge-needle units are generally packaged in a tamper resistant container. Often the container will use a metal shield at the plunger ends of the barrels to keep unscrupulous individuals from surreptitiously gaining access to the contents of the unit. The special packaging used is relatively costly and increases the actual cost of each cartridge-needle unit. Further, the present systems are not well suited for preventing inadvertent needle sticks, a serious health concern.

SUMMARY OF THE INVENTION

The present invention is directed to an enclosure unit specially adapted for use with conventional cartridge-needle units to create a low-cost disposable syringe. Several of the enclosure units can be molded as a set which act as the packaging for the cartridge-needle units. The syringes can be separated for use at frangible attachment points connecting the enclosure units.

The cartridge-needle unit is of the type having a hollow barrel with a needle assembly mounted to one end and a piston mounted within the hollow barrel. The enclosure unit includes a body section sized to house the barrel, a stem section at one end of the barrel sized to house the needle assembly which may include a sheath or cover, and an end section or cap at the other end of the body section. The enclosure unit is preferably a one-piece molded item with the end cap connected to the body section by integral hinge. The stem section is frangibly attached to the body section so that it can be removed to be used as a plunger. The tip of the removed stem section is connected to the piston to move the piston within the barrel during use.

After use, the barrel of the cartridge-needle unit is pulled back through the body section so that the needle is completely housed within the body section. The body section includes one or more radially inwardly extending spring fingers, or like structure, near the plunger end of the body section. The spring fingers engage the hub of the needle assembly and keep the needle assembly from being withdrawn from the body section. This permits a safe disposal of a used syringe.

The enclosure is preferably molded as a set of enclosure units connected to one another by frangible connections. A set of conventional cartridge-needle units can thus be placed within each of the enclosure units in the set for storage, shipping and distribution to the end user. The syringe set needs no special packaging, thus substantially reducing cost.

One of the primary advantages of the invention is that it eliminates the need for separate, and costly, safety packaging for cartridge-needle units. The enclosure units not only provide safety packaging but also eliminate the need for cartridge-needle unit holders when dispensing the medication. In addition, the enclosure unit is adapted to permit the needle to be withdrawn into the body section of the enclosure unit for safe disposal after use. These advantages are all achieved at relatively low cost through the use of enclosure units made of one, or preferably at most two, molded parts without requiring any substantial modification of conventional cartridge-needle units.

The invention can be carried out using an enclosure unit in which the internal diameter along at least one-third of the length of the body section from its needle end is a constant diameter. This eliminates any need for a shoulder or other inward projection which would prevent the cartridge-needle unit from potentially passing through the opening at the needle end once the stem section has been removed. The body can be fabricated with or without a shoulder. To accommodate this, the plunger end of the body section is secured to the barrel of the cartridge-needle unit, such as with a friction fit or using an adhesive. To permit conventional cartridge-needle units to be activated, the plunger end of the body section in one embodiment is connected to the remainder of the body section by, preferably, a pair of relatively thin, flexible teathers; this permits the plunger end to be pushed toward the remainder of the body section, thus driving the barrel towards the needle assembly prior to removing the stem section. After the cartridge-needle unit is activated, the plunger end is twisted causing the teathers to break. The stem can then be used as a plunger to drive the piston and administer the contents of the barrel. The user then pulls the barrel from the body section until the spring fingers engage the annular recess adjacent the rear shoulder of the hub, thus halting movement as with the embodiment described above.

In another alternative embodiment of the invention, the enclosure unit remains the same in structural aspects except the spring fingers are replaced by a detent and overlapping sleeve means where the detent is molded as part of the body section and used to secure the hub portion of the cartridge-needle unit when biased inward by an overlapping sleeve.

In this embodiment, the sleeve is molded to the proximal end of the body section and is connected to the body section by frangible connections. To activate the overlapping sleeve means of the enclosure unit, the sleeve is pushed toward the distal end of the body section to activate the sleeve around the body. The inner diameter of the sleeve is approximately equal to the outer diameter of the body section. As the sleeve is forced towards the distal end of the body section, the sleeve engages the body section at its proximal end and centers via assembly ramps and passes onto the body section. A detent and catch pin molded integral to the body section are biased inward as the sleeve passes over until the detent and catch pin are captured in a detent relief chamber and catch pin aperture, respectively, where the detent and catch pin are in an unbiased position and the sleeve is in the engaged position. The cartridge-needle unit is then inserted into the enclosure unit through the opening of the end portion. The cap is subsequently heat sealed to provide a tamper-resistant enclosure unit ready for shipping.

Once in the hands of the user, the removable end portion located at the proximal end of the sleeve can be removed by twisting causing the frangible connections to break. The removable end portion is removed and the proximal end of the barrel portion of the cartridge-needle unit is exposed and activated. This allows the medication to be injected into the patient. Following activation of the cartridge-needle unit, the catch pin is locked into the distal catch cavity portion of the catch pin aperture, securing the sleeve in a position which biases the detent inwardly where it contacts the barrel portion of the cartridge-needle unit. Following administration of the injection, the user pulls the barrel from the body section until the annular recess adjacent the rear shoulder of the hub engage the shoulders at the proximal end of the body section. In this position, the shoulders prevent further movement towards the proximal end of the body section and the inwardly biased detent prevents distal movement of the hub section. The hub is locked into position with the needle safely enclosed in the body section for safe disposal.

The hub cap described in U.S. patent application Ser. No. 07/580,931 filed Sep. 11, 1990 herein incorporated by reference, discloses an appropriate hub cap for use with alternative types and sizes of cartridge needle units.

In an alternative embodiment of the invention, the hollow body portion includes two stabilizing tabs which are located opposite one another and are molded integral with the hollow body portion near its proximal end. The connection between the hollow body portion and the stabilizing tabs is in the form of a flexible hinge which allows the stabilizing tabs to be pivoted between an unlocked position and a locked position. The hollow body portion is molded having the stabilizing tabs in the unlocked position where they extend outwardly and are hinged to the hollow body portion at their upper inside surface. When a cartridge needle unit is positioned inside the hollow body portion, the stabilizing tabs can be pivoted about the hinge so that the stabilizing tabs abut the barrel of the cartridge needle unit on either side and secure it into place. The stabilizing tabs can be locked into position by engaging a notch located on the stabilizing tab with a shoulder of the fingers located on the proximal end of the hollow body portion. When the stabilizing tabs are in the locked position, the barrel is secured in place and restricted from lateral or longitudinal movement.

In the preferred embodiment, the invention is intended for use with sterile cartridge-needle units, therefore, the enclosure unit of the invention need not be sterile thus reducing cost.

Other features and advantages of the invention will appear from the following description in which the preferred embodiments have been set forth in detail in conjunction with the accompanying drawings.

BRIEF DESCRIPTION OF THE DRAWINGS

FIG. 1 is a front view showing an enclosure unit set and an associated set of cartridge-needle units prior to insertion of the cartridge-needle units into the hollow interiors of the enclosure units;

FIG. 2 is a side view of an enclosure unit of FIG. 1 illustrating the hinged connection of the end section of the enclosure unit to the body section of the enclosure unit;

FIG. 5 is a front view of the safety syringe of FIG. 3, illustrating various components of the cartridge-needle unit in dashed lines and with a portion of the stem section of the enclosure unit broken away to show internal detail;

FIG. 5A is an enlarged view showing the frangible connection between the stem and body sections of the enclosure unit of FIG. 5;

FIG. 6 illustrates the safety syringe of FIG. 5 with the stem and end sections removed from the body section and illustrating the activation of the cartridge-needle unit by pushing the plunger end of the barrel into the body section;

FIG. 7 illustrates mounting the tip of the stem section to the threaded mounting post of the plunger.

FIG. 14 is a front view of the safety syringe of the embodiment of FIG. 13 showing a partial cross-section view broken away to show internal detail, illustrating the sleeve portion in an unengaged condition having the detent and catch pin in a neutral and unbiased position;

FIG. 14a is an enlarged view of the cross-section view provided in FIG. 14 showing the frangible connection between the body section and the sleeve and the frangible connection between the sleeve and the removable end portion, the sleeve illustrated showing the detent relief chamber and the catch pin aperture;

FIG. 15 is a left side view of a portion of the safety syringe of FIG. 14 illustrating the detent and tongue located on the body section and partially surrounded by a hollow channel with the assembly ramps at the proximal end of the body section;

FIG. 16 is a front view of the syringe set of FIG. 13 showing the enclosure units with the sleeve in the engaged position and an associated set of cartridge-unit units prior to insertion of the cartridge-unit units into the hollow interiors of the enclosure units;

FIG. 17 a side view of an enclosure unit of the embodiment shown in FIG. 16 illustrating the hinged connection of the end cap of the enclosure unit to the body section of the enclosure unit;

FIG. 27 shows an alternative embodiment of the safety syringe having stabilizing tabs in the unlocked position;

FIG. 28 is a side view of the embodiment shown in FIG. 27 illustrating a stabilizing tab in the unlocked position illustrating the concave curved surface of the stabilizing tab;

FIG. 29 is a partial cut-away view of the embodiment of FIG. 27 showing the hinged movement of the stabilizing tabs from the unlocked position, shown in broken lines, to the locked position where a notch in the stabilizing tab engages the upper shoulders of the fingers; and FIG. 30 is a cross-section view along lines AA of FIG. 32 showing the stabilizing tabs in the locked position with the curved surface of the stabilizing tabs abutting the outer diameter of the barrel portion of a cartridge needle unit located in the hollow body portion of the safety syringe.

DESCRIPTION OF THE PREFERRED EMBODIMENT

Figure 3:
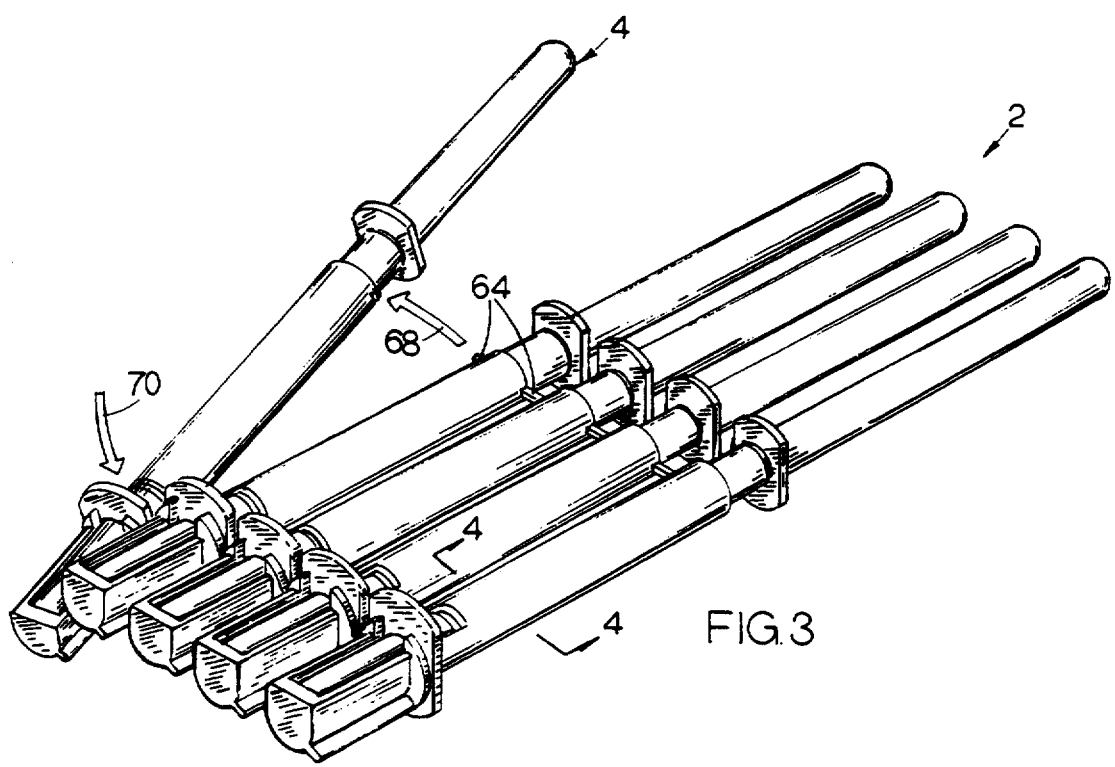
FIG. 3 is a perspective view of a syringe set of FIG. 1 after assembly with the end sections of the enclosure units covering the plunger ends of the barrels of the cartridge-needle units and illustrating breaking the frangible connections between two adjacent syringes.

FIG. 3 illustrates a set 2 of safety syringes 4. The set 2, as suggested in FIG. 1, is made up of a set 6 of enclosure units 8 and a set 10 of cartridge-needle units 12. Cartridge-needle units 12 are preferably generally conventional in construction. One such cartridge-needle unit is made by Winthrop Brean of New York, N.Y. under the trademark CARPUJECT. Each unit 12 includes a glass barrel 14 having a piston 16 at a plunger end 18 and a necked down portion 20 at a needle end 22. A needle assembly 24 is mounted to necked down portion 20 of barrel 14. Needle assembly 24 includes a needle 26, see FIG. 8, mounted to an extension 28 of a needle mount 30. Needle mount 30 includes a ribbed coupler 32 and a hub 34. Needle assembly 24 is mounted to necked down portion 20 by needle mount 30 at hub 34. Needle 26 is covered by a removable sheath 36.

Enclosure unit 8 includes a hollow body section 38 having a plunger end 40 and a needle end 42. Unit 8 also includes a stem section 44 extending from a necked down portion 46 of body section 38 at needle end 42. Stem section 44 is also hollow and is sized to enclose sheath 36 covering needle 26. Body section 38 and stem section 44 are a one-piece molding connected at frangible connections 48 adjacent a flange 50 at the base of stem section 44 and necked down portion 46 at the end of body section 38.

Enclosure unit 8 also includes an end section or cap 52. In the preferred embodiment of set 6 of enclosure units 8, enclosure units 8, including body section 38, stem section 44 and cap 52, is a one-piece molded item. Caps 52 are connected to flanges 54 at plunger ends 40 of body sections 38 by hinges 56. Since the entire barrel 14 does not fit within body section 38, but a portion extends past the plunger end 40, pivotal end section 52 has a open side 58 to permit end section 52 to be pivoted over plunger end 18 of barrel 14. After doing so, a flange 60 of end section 52 is secured to flange 54 at plunger end 40, such as by ultrasonic welding techniques.

Set 2 of safety syringes 4 are thus provided with their own safety packaging in the form of set 6 of enclosure units 8. Specialized and costly packaging for units 12 is not needed. Tampering is discouraged since any tampering would be evident by the resulting breaking of frangible connections in the bond between flanges 52, 56. Further, the ends 62 of end sections 52 are relatively thick plastic to substantially prevent unauthorized access to pistons while cap 52 is in the closed or sealed position of FIG. 3.

Enclosure units 8 are connected to one another at frangible connections 64 and 66. To use a safety syringe 4, the safety syringe is separated from the remaining safety syringes by severing frangible connections 64,66 as illustrated by arrows 68,70 in FIG. 3.

FIG. 5 is a front view of the safety syringe 4 of FIG. 3. The various components of cartridge-needle unit 12 are shown in dashed lines to illustrate their relative positions within enclosure 8.

Figure 10:
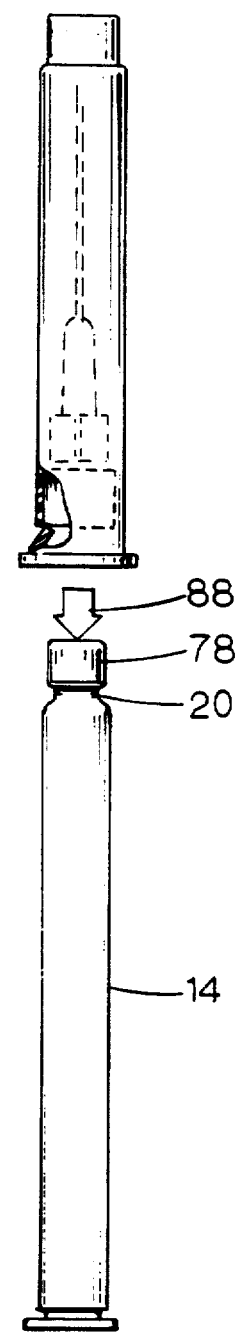
FIG. 10 illustrates the disengagement of the barrel of the cartridge-needle unit from the hub of the needle assembly for disposal.

FIG. 6 illustrates safety syringe 4 of FIG. 5 with stem section 44 removed through the breaking of frangible connections 48 illustrated in FIG. 5A. Also, FIG. 6 suggests the axial movement of barrel 14 in the direction of arrow 72 thus activating cartridge-needle unit 12. This movement is suggested by the change in the size of the annular recess 74 formed at the rear shoulder 76 of hub 34 and necked down portion 20 of barrel 14 at needle end 22. (Compare FIGS. 5 and 6.) Hub 34 of needle assembly 24 is prevented from moving in the direction of arrow 72 by the engagement of a front shoulder 75 of hub 34 with a shoulder 77 of body section 38 adjacent necked down portion 46. With the particular cartridge-needle unit 12 used in this embodiment, such movement permits the base end, not shown, of needle 26 to puncture a diaphragm, not shown, carried by an end cap 78, shown in FIG. 10, mounted to necked down portion 20. Doing so permits the contents of barrel 14 to flow through needle 26 when piston 16 is forced through barrel 14. To do so, the threaded tip 80 of stem section 44 is mounted to a threaded mounting post 81 extending from piston 16 as suggested in FIG. 7. Stem section 44 with its flange 50 acts as a stem or plunger for delivery of the contents of barrel 14 through needle 26.

Figure 8:
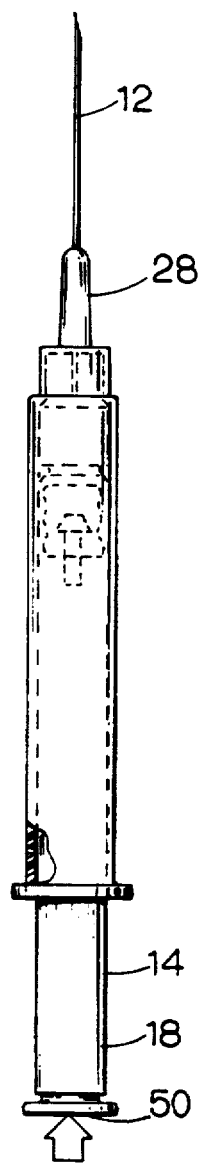
FIG. 8 illustrates the safety syringe of FIG. 7 after the sheath has been removed and the injection has been given.
Figure 9:
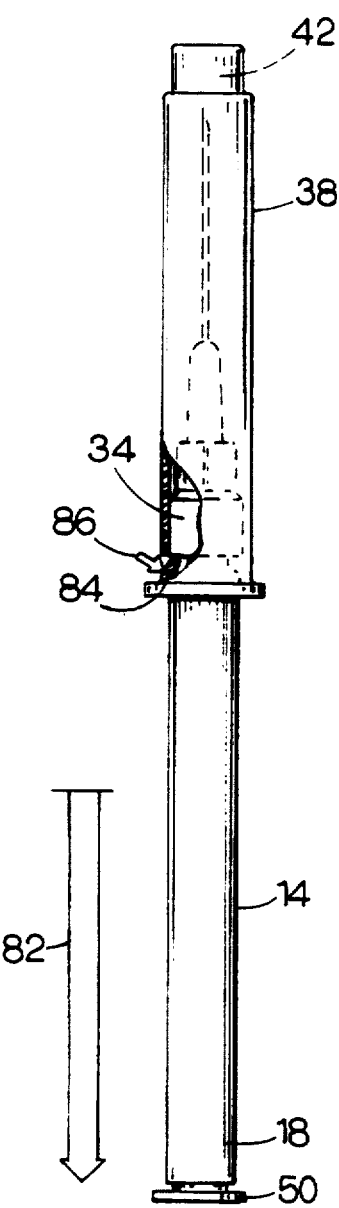
FIG. 9 illustrates the withdrawal of the barrel from the body section until the rear shoulder of the hub engages the inwardly extending spring finger adjacent the plunger end of the body section, the spring finger located so that the entire needle is within the body section at this position.

FIG. 8 illustrates stem section 44 fully within barrel 14 with the contents of barrel 14 fully delivered. Though the spent syringe could be disposed of as is, it may be dangerous to do so with needle 26 exposed. To place needle 26 in its safe position, the user grasps the plunger end 18 of barrel 14 and pulls in the direction of arrow 82. When barrel 14 reaches the position of FIG. 9, an inwardly biased securing means, specifically a spring finger 84 formed as part of body section 38, pivots inwardly as suggested by arrow 86 to enter annular recess 74 and engage rear shoulder 76 of hub 34. This prevents the further withdrawal of needle assembly 24 (minus sheath 36) from body section 38. The syringe unit in the safe position of FIG. 9 can be disposed as is. With the particular cartridge-needle unit 12 of the preferred embodiment, further movement of barrel 14 in the direction or arrow 88, see FIG. 10, causes the disengagement of end cap 78 from within hub 34 so that the used syringe can be disposed of as two components, but in a safe manner.

Figure 4:
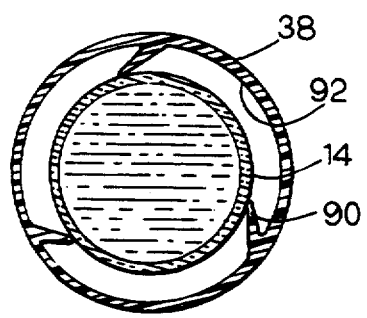
FIG. 4 is a cross-sectional view taken along line 4—4 of FIG. 3, showing the flexible centering tabs which accommodate Different size barrels.

FIG. 4 illustrates the provision of three resilient centering tabs 90 extending from the inner surface 92 of body section 38 adjacent spring finger 84. Centering tabs 90 center barrel 14 and also keep cartridge-needle unit 12 from slipping out plunger end 40 of body section 38 when end section 52 is removed. Centering tabs 90 likewise engage hub 34 when the needle is in the safe position of FIGS. 9 and 10 to keep the needle from inadvertently moving back through the open needle end 42 of body section 38.

Figure 11:
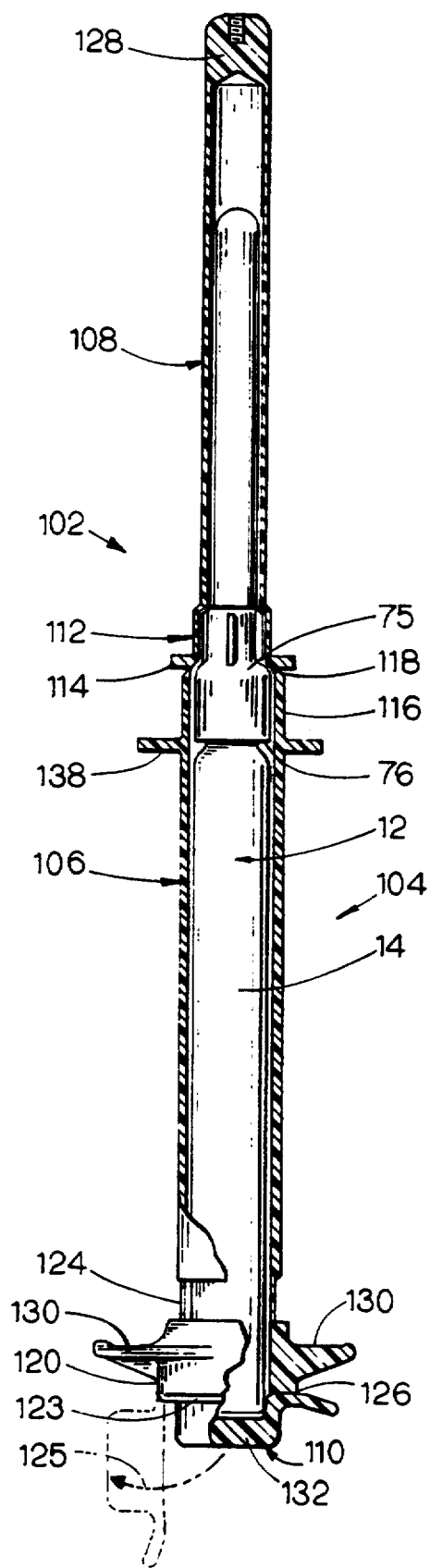
FIG. 11 is a front, partial cross-sectional view of an alternative embodiment of the safety syringe of FIG. 3.
Figure 12:
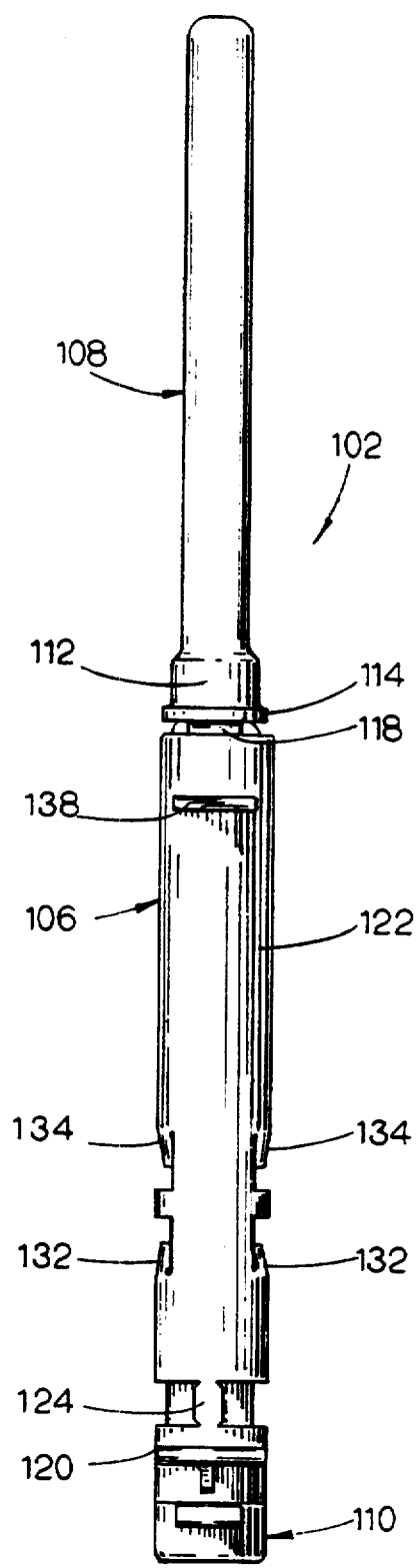
FIG. 12 is a right side view of the safety syringe of FIG. 11.
Figure 13:
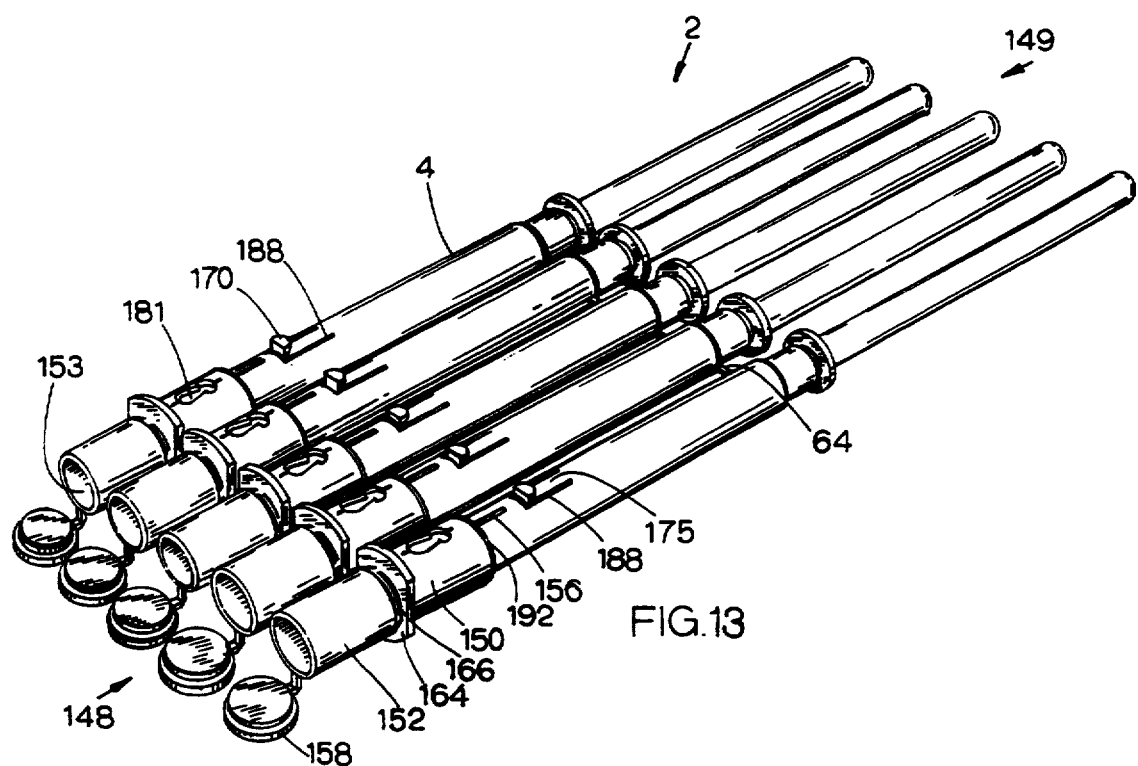
FIG. 13 is a perspective view of an alternate embodiment of the invention showing a syringe set as molded having the sleeve in the non-engaged position and showing the sleeve molded on the proximal end of the body section and connected by frangible connections, the removable end portions frangibly connected to the proximal end of the sleeve and having end caps in the open hinged position.

FIGS. 11 and 12 show an alternative embodiment of the safety syringe 4. Syringe 102 uses cartridge-needle unit 12. Safety syringe 102 includes an enclosure unit 104 having a body section 106, a stem section 108 and an end section or cap 110. Enclosure unit 104 is similar to enclosure unit 8 but with the distinctions described below. With the embodiment of FIG. 1, necked down portion 46 is a part of body section 38. With the embodiment of FIG. 11, an intermediate diameter portion 112 is a part of stem section 108. A flange 114 is at the base of stem section 108 and is between intermediate diameter portion 112 and the needle end 116 of body section 106. The connection between stem section 108 and body section 106 is through frangible connections 118. Once stem section 108 is removed, typically by twisting relative to body section 106, the inner diameter of body section 106 from its needle end 116 rearwardly, that is, towards end section 110, is a constant diameter for at least one-third of the length of body section 106.

To keep cartridge-needle unit 12 from falling out of open needle end 116 once stem section 108 has been removed, plunger end 120 of body section 106 is secured to plunger end 18 of barrel 14. This can be by frictional engagement, by use of an adhesive, or similar means. The plunger end 120 of body section 106 is secured to the remainder 122 of body section 106 by a pair of flexible teathers 124. Teathers 124 are flexible enough to permit plunger end 120 to be driven towards remainder 122 when it is desired to activate cartridge-needle unit 12. Once this is done, stem section 108 is removed and end section 110 is pivoted about hinge 123 in the direction of arrow 125, thus breaking the heat seal at 126. This provides access to piston 16 so that the threaded tip 128 of stem section 108 can be secured to the threaded mounting post 82 of piston 16 to deliver the contents of barrel 14.

To pull needle 26 back into body section 106, the user grasps radially extending ears 130 extending from plunger end 120 and twists to sever the frangible connections at teathers 124. Barrel 14 is then pulled back through body section 106 until rear shoulder 76 contacts first spring fingers 132. Continued pulling of plunger end 120 causes barrel 14 to be separated from hub 34 as in FIG. 10. A second pair of spring fingers 134 engage the front shoulder 75 of hub 34 to substantially prevent the inadvertent movement of needle 26 back through open needle end 116. The tapered shape of front shoulder 75 allows the insertion of cartridge-needle unit 12 into body section 106 but supplies sufficient retarding force to keep the needle within body section 106 after use.

As with end section 52, end section 110 has a thick end 132, typically 2.5 mm thick. Making enclosure units 8, 104 of a suitable plastic, such as polypropylene or polyethylene, provides the necessary resilience and strength at a reasonable price. Enclosure unit 104 is preferably provided as a set of enclosure units with the frangible connections through ears 130 and frangible connecting pieces 138. Cartridge-needle units 12 are preferably of the type in which axial movement is undertaken to activate the unit; however, cartridge-needle units which do not need such activation may be used as well. In such cases, teathers 124 could be replaced by simple frangible connections. Although it is desired that conventional cartridge-needle units 12 be used, some small modifications may be desirable. For example, the diameter of all or most of sheath 36 may be reduced to permit an increase in the wall thickness of stem section 44 used as the plunger stem.

FIGS. 13–29 show an alternative embodiment of the safety syringe 4. Referring now to FIG. 16, the safety syringe 4 of the alternative embodiment incorporates an alternative means for securing the needle cartridge unit 12 by its hub 34 within the hollow body section 38. A sleeve 150 used in conjunction with a detent 174 and a catch pin 170 along with shoulders 202 located at the proximal end of the body section 190 form an alternative securing means of securing the hub 34 in the hollow body section 38 in function similar to the spring finger 84 of the embodiment described above and shown in FIGS. 1–10 and the spring fingers 132 and 134 of FIGS. 11–12.

Figure 20:
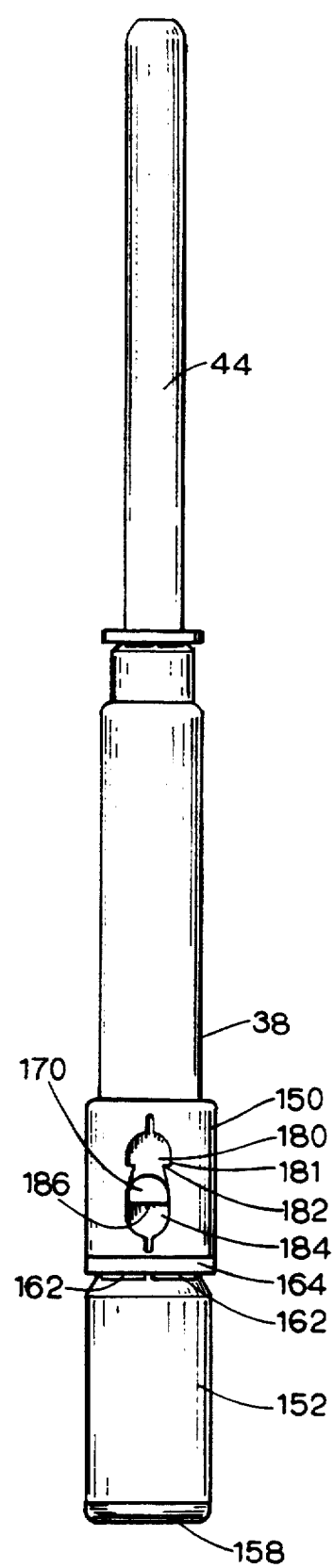
FIG. 20 is a right side view of the safety syringe of FIG. 18 showing the catch pin inside the proximal catch cavity of the catch pin aperture.

Referring now to FIG. 15, the safety syringe 4 is molded with the sleeve 150 at the proximal end of the hollow body section 38. The sleeve 150 is affixed to the hollow body section 38 by frangible connections 192. At the proximal end of the sleeve 150, a removable end portion 152 is frangibly connected. A cap 158 is hinged to the removable end portion 152 by a hinge 160. As shown in FIG. 16 and FIG. 16a, the sleeve 150 comprises a detent relief chamber 178 and a catch pin aperture 181. The catch pin aperture 181 includes a distal catch cavity 180 and a proximal catch cavity 184. As shown in FIG. 20, the distal catch cavity 180 and the proximal catch cavity 184 are separated by a catch hook 182. A pair of fingers 164 extend outwardly from the proximal end of the sleeve 150. At the proximal end 148 of the sleeve 150, frangible connections 166 attach the removable end portion 152 to the sleeve 150 and are separated by gaps 162 to help make the removable end portion 152 easy to disengage from the sleeve 150 by twisting.

As shown in FIG. 15, the hollow body portion 38 is formed having a catch pin 170 protruding outwardly and surrounded by a hollow channel 188 which allows the catch pin 170 to bias inwardly towards the center axis of the hollow body 38 by appropriate external force. A slot 156 is located near the body section proximal end 190. FIG. 15 shows a syringe set 2 having a plurality of safety syringes 4 connected by frangible connections 64. Also located on the hollow body 38 is a detent 174 partially surrounded by a second hollow channel 172 as shown in FIG. 17.

A cartridge needle unit 12 can be inserted into the safety syringe 4 through the opening 153 located in the removable end portion 152 when the cap 158 is in the open position. The body section 38 can be formed having slots 156 to allow the body section proximal end 190 to expand circumflexually to accommodate the cartridge-needle unit 12. The cap 158 can be closed without activating the cartridge-needle unit 12. To secure the cartridge-needle unit 12 inside the safety syringe 4 for shipping purposes, cap 158 can be heat sealed to the end portion 152 to provide a tamper proof package.

To engage the sleeve 150 with the body section 38, the frangible connection 192 between the body section 38 and the sleeve 150 is broken as the sleeve 150 is pushed up onto the body section 38 towards the distal end 149 of the safety syringe 4. The body section proximal end 190 includes assembly ramps 154 which allow the sleeve 150 to make a smooth transition onto the outer surface of the body section 38. To secure the sleeve in the fully activated position, the sleeve 150 travels towards the distal end 149 over the detent 174 and catch pin 170 forcing them to bias inwardly through the hollow channels 172, 188 respectively, until the detent 174 is captured in the detent relief chamber 178 and the catch pin 170 is captured in the catch pin aperture 181 are in the natural, unbiased condition.

Figure 18:
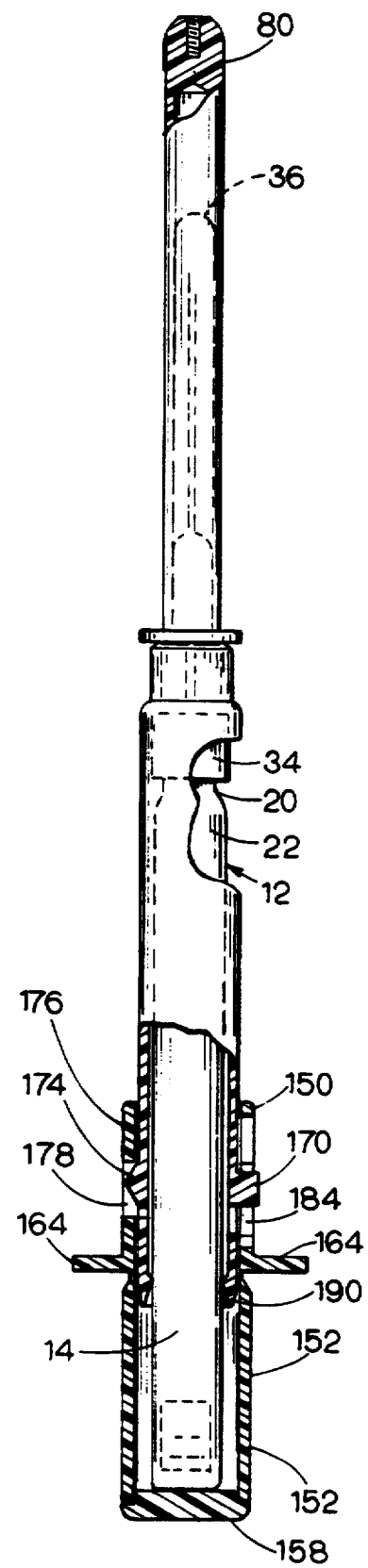
FIG. 18 illustrates a safety syringe of the set shown in FIG. 16 having the cap closed and a cartridge needle unit enclosed therein and providing a partial cross-sectional view showing the sleeve in the activated position over the proximal end of the body section with the catch pin positioned in the proximal catch cavity of the catch pin aperture and the detent positioned in the detent relief chamber, both the detent and the catch pin in their neutral, unbiased condition.

The detent 174 is located on the proximal end of resilient tongue 176 which is integral with the body section 38 and surrounded by a hollow channel 178. This structure allows the detent to bias inwardly as the sleeve 150 passes over it. Once the detent 174 is adjacent to the detent relief chamber 178, the force biasing the detent inwardly is removed allowing the detent 174 to return to its natural, non-bias state as shown in FIG. 18. Similarly, the catch pin 170 is located on a resilient catch pin tongue 175 and biases inwardly as the sleeve 150 passes over it until the catch pin 170 can extend into the catch pin aperture 181 by returning to its natural state when the inward biasing force caused by the sleeve 150 is relieved.

Figure 19:
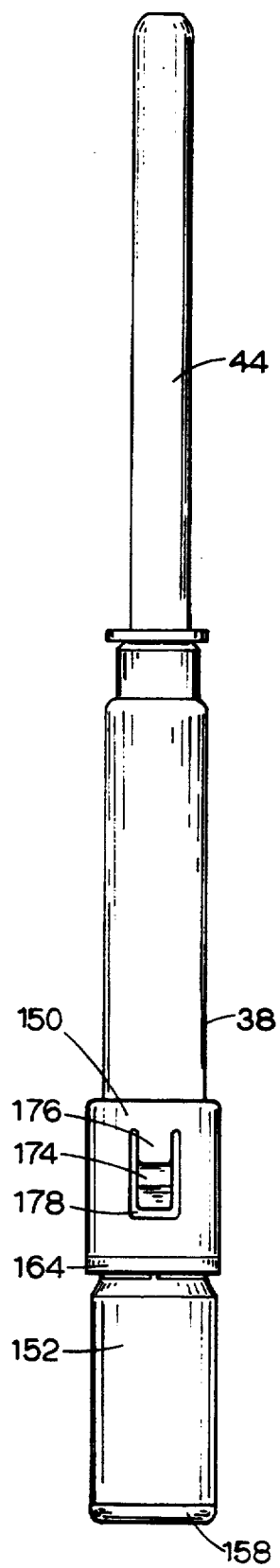
FIG. 19 is a left side view of the safety syringe of FIG. 18 showing the detent positioned in the detent relief chamber on the proximal end of the tongue.

FIG. 18 shows a cross-section of the sleeve in the activated condition where the detent 174 is extended into the detent relief chamber 178 and the catch pin 170 is extended into the proximal catch cavity 184 of the catch pin aperture 181. FIG. 19 shows a left side view of the sleeve in the engaged position with the detent 174 lying just below the tongue portion 176 as it extends down into the detent relief chamber 178. Similarly, FIG. 20 shows a left hand view of FIG. 18 illustrating the catch pin 170 in the catch pin aperture 180.

Figure 22:
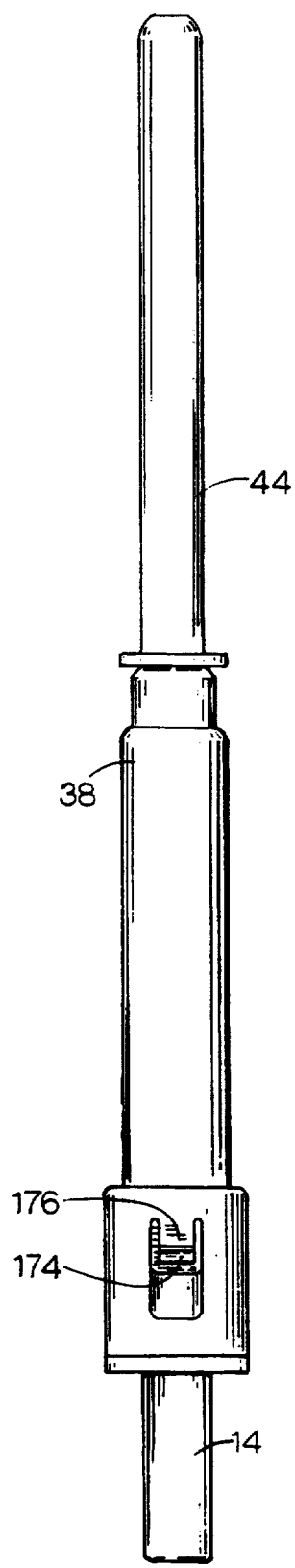
FIG. 22 is a left side view of the safety syringe illustrated in FIG. 21 showing the tongue overlapping the detent and biasing it inwardly.
Figure 21:
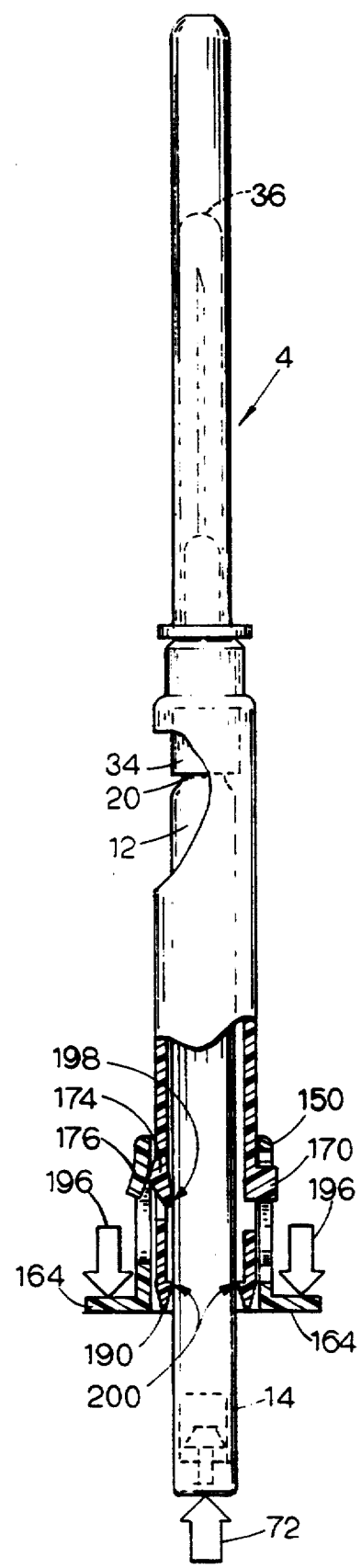
FIG. 21 is a front partial cross-section view of the safety syringe of FIG. 18 showing the end portion removed and the detent being biased inwardly by the tongue portion of the sleeve and engaging with the barrel portion of the cartridge-needle unit, the arrows indicating the activation force applied to the cartridge-needle unit by pushing the plunger end of the barrel into the body section as the sleeve portion is locked into place.
Figure 23:
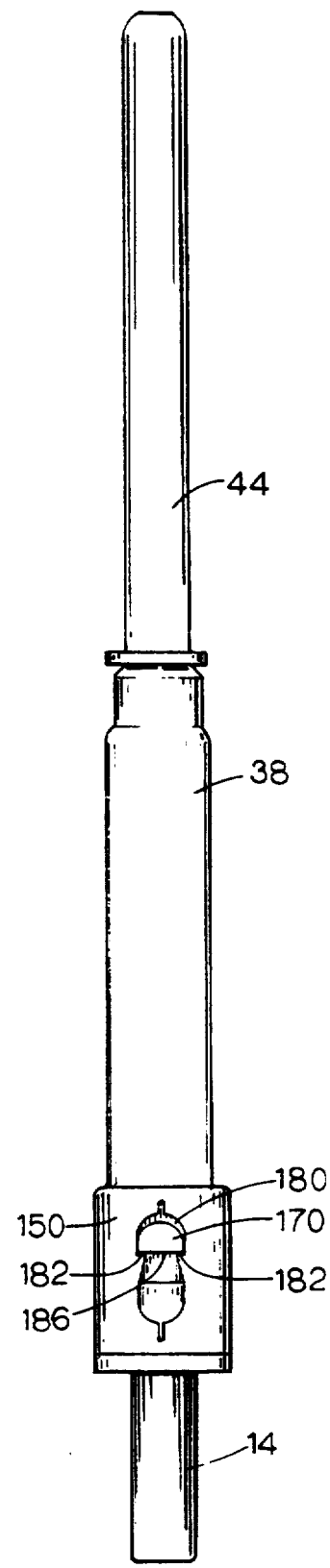
FIG. 23 is a right side view of the safety syringe illustrated in FIG. 21 showing the sleeve locked into position where the catch pin is positioned in the distal catch cavity on the distal side of the catch hooks.
Figure 24:
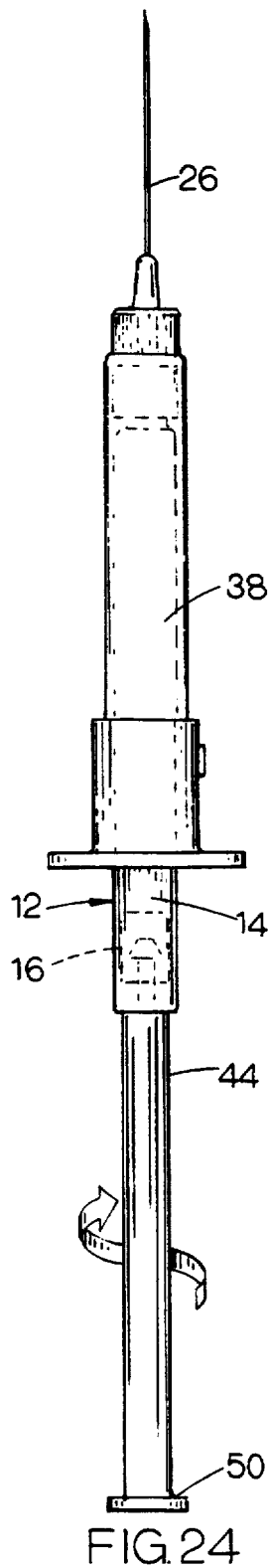
FIG. 24 illustrates the tip of the stem section of the safety syringe in FIG. 21 mounted to the threaded insert of the piston using a twisting motion.

FIGS. 21–23 show a partial cross-section view, a left-hand view, and right-hand view, respectively, during activation of the needle-cartridge unit. As the sleeve 150 is forced in the distal-to-proximal direction by pressure exerted on the fingers 160 as depicted by the arrows 196, the sleeve 150 moves in the proximal direction until the catch pin 170 is captured by the distal catch cavity 180 and locks into place as depicted in FIG. 23. The catch hooks 182 abut the catch pin 170 at its lower surface 186 and prevent it from traveling in the distal-to-proximal direction once it is captured in the distal catch cavity 180. In the activated position, the detent 174 is biased inwardly from the force exerted by the tongue 176 as it overlaps the detent 174 as shown in FIGS. 21 and 22. The inward bias of the detent 174 may cause the detent to engage the barrel 14 at a friction point 198 to help secure the cartridge-needle unit 12 inside the hollow body portion 38 so that the drug can be administered by pushing the piston 16 towards the needle end 22 of the cartridge-needle unit 12 as depicted by the arrow 72. Additionally, the body section proximal end 190 may come in contact with the barrel 14 at friction points 200 to further stabilize the barrel 14. As previously described, the threaded tip 80 of stem section 44 is mounted to a threaded insert of the piston 16 as suggested in FIG. 24. Stem section 44 with its flange 50 acts as a stem or a plunger for a delivery of the contents of barrel 14 through needle 26.

Figure 25:
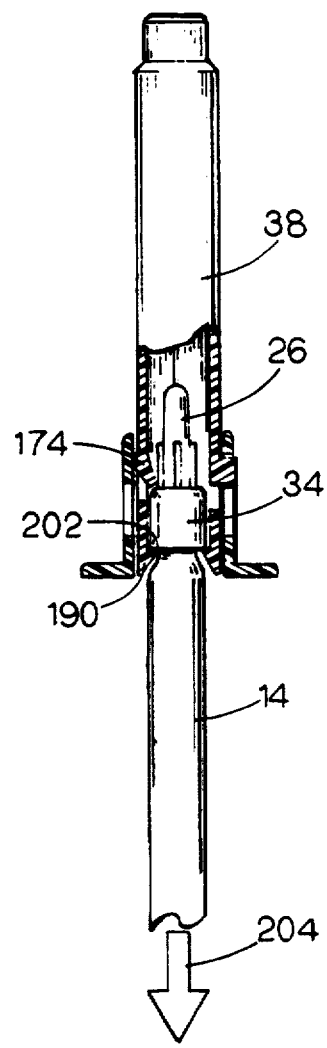
FIG. 25 illustrates the withdrawal of the barrel from the body section of the safety syringe in FIG. 21 until the engagement of the rear shoulder of the hub with the shoulders located on the proximal end of the body section combine with the detent biasing inwardly to restrain the cartridge-needle unit from movement in the proximal-to-distal or distal-to-proximal direction so that the hub is locked and the entire needle is positioned within the body section.

After the contents of the barrel 14 are administered, the barrel 14 is pulled in the distal-to-proximal direction as shown by arrow 204 in FIG. 25. Barrel 14 moves in the distal-to-proximal direction until shoulders 202, located at the body section proximal end 190, engage the proximal end of the hub 34 as shown in FIG. 25. The inwardly biasing force exerted by the tongue 176 against the detent 174 causes the detent 174 to swing into the fully biased position through the hollow channel 172 such that it extends inwardly on the distal side of hub 34 and prevents any proximal-to-distal movement as shown in FIG. 25. The hub 34 is then in the fully locked position and the needle 26 is safely contained in the hollow body 38 and ready for safe disposal.

Figure 26:
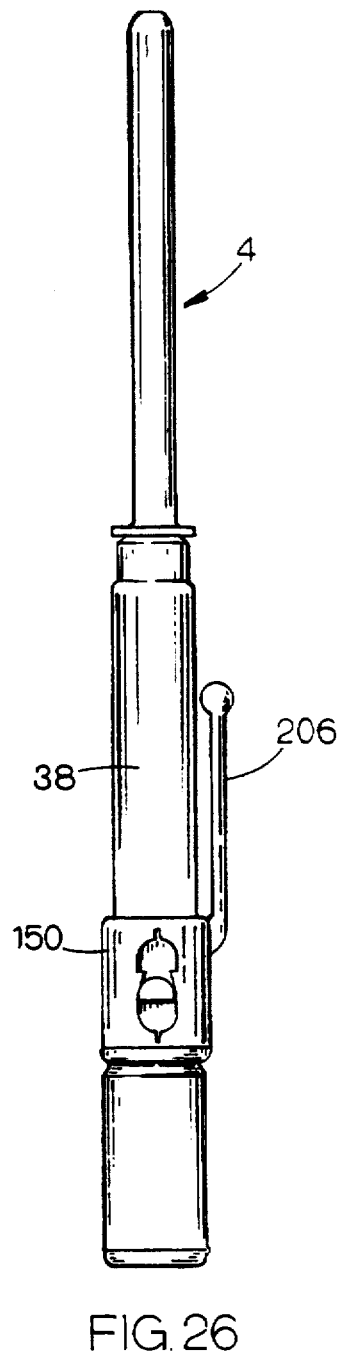
FIG. 26 shows an alternative embodiment of the safety syringe in FIG. 20 having a pocket clip secured to the sleeve.

FIG. 26 shows still an additional embodiment of the invention where a pocket clip 206 is affixed to the sleeve 150 to allow the safety syringe 4 to be securely transported in a pocket.

A further embodiment of the invention is shown in FIGS. 27–30. Referring to FIGS. 27–28, the safety syringe 4 of the alternative embodiment incorporates a hollow body portion 38 having two stabilizing tabs 21 8 connected to the hollow body portion 38 by flexible hinge 220. The stabilizing tab 218 is located in a hollow channel 222 and can be pivoted about the hinge 220 into the hollow channel 222. Each stabilizing tab 218 has a tapered outer edge 236 and a notch 232 shown in FIG. 27. As shown in FIG. 31, the stabilizing tab 218 has a concave surface 224 which faces downwardly when the stabilizing tab is in the unlocked position shown in FIGS. 27 and 28. A pair of fingers 216 are located at the proximal end of the hollow body portion 38 and extend outwardly. Each finger 216 has a shoulder 234 which defines the proximal side of the hollow channel 222.

FIG. 29 shows the stabilizing tabs 218 being used to secure the barrel 14 of a cartridge needle unit 12. When a cartridge needle unit 12 is disposed in the hollow body portion 38 of safety syringe 4, each stabilizing tab 218 can be pivoted about the hinge 220 from an unlocked position 230, shown in broken lines to a locked position 228 as shown in FIG. 29. The curved surface 224 of the stabilizing tab 21 8 is concave with the concave curvature contacting the outer diameter of a barrel 14 of a cartridge needle unit 12 when in the locked position 228. Therefore, in the locked position 228, the curved surface 224 of the stabilizing tab 21 8 conforms to the outer surface of the barrel 14 as shown in FIG. 30. The stabilizing tabs 228 are locked into position by fully pivoting about the hinge 220 into the hollow channel 222 until the notch 232 engages the shoulder 234 of the finger 216 as shown in FIG. 29.

It is intended that both of the stabilizing tabs 218 be pivoted into the locked position 228 before the cartridge needle unit 12 is loaded. The tapered outer edge 236 serves two functions. First, as the stabilizing tabs 218 are pivoted about the hinge 220, the tapered outer edge 236 allows the stabilizing Tab 218 to clear the finger 216 as it pivots past it. Thus, the notch 232 can engage the upper shoulder 234 of the finger 21 6 to secure the stabilizing tab 218 into the locked position 228. Second, when the stabilizing tab 218 is in the locked position 228, the tapered outer edge 236 helps to guide and center the cartridge needle unit 12 into the hollow body portion 38 when the cartridge needle unit 12 is inserted into the proximal opening 153 of the removable end portion 152. FIG. 29 shows the barrel 14 positioned inside the hollow body portion 38, the cross-section showing half of the stabilizing tab 21 8 in the locked position 228 with the broken line 240 illustrating wing 242 curving rearward around the back of the barrel 214, Once the cartridge needle unit 12 is loaded into the safety syringe 4, the barrel 14 is fully contained and centered within the hollow body portion 38 and the cap 158 can be pivoted about the hinge 160 to close the proximal opening 238 of the removable end portion 152. The cap 158 can then be heat sealed in the closed position as shown in FIG. 29 to create a tamper resistance package. Like the other embodiments previously discussed, the cap 158 has a sufficient thickness to preclude vandals or other parties from inserting needles through the cap 158 to compromise the contents of the cartridge needle unit 12.

Other modifications and variations can be made to the disclosed embodiments without departing from the subject of the invention as defined in the following claims. For example, the enclosure unit can be sterilized to facilitate use of cartridge-needle units without a needle sheath, thereby producing economy of parts and materials.

What is claimed is:

1. A disposable safety syringe comprising:
 a cartridge-needle unit including a hollow barrel, a piston mounted within the barrel, a needle assembly mounted to an end of the barrel, the needle assembly including a needle and a hub having a front shoulder and a radially extending rear shoulder; and
 a hollow enclosure unit sized for housing the cartridge-needle unit therein, the enclosure unit comprising:
  a body section for housing the barrel, the body section having a plunger end and a needle end having an opening so that the needle may pass therethrough, the needle end also having a necked down portion sized smaller than the hub so that the hub cannot pass through the opening, the cartridge-needle unit being at least partially positioned within the body section, and the body section having a cross-sectional shape generally larger than a cross-sectional shape of the cartridge-needle unit so that the cartridge-needle unit is slidably movable within the body section;
  a stem engageable with the piston to enable a user to drive the piston along the barrel from the plunger end of the barrel assembly;
  and means for engaging said hub in said body section, thereby securing said needle assembly in the body section with the needle fully within the body section, and preventing further movement of the cartridge-needle unit from a safe position.

2. A disposable safety syringe comprising:
 a cartridge-needle unit including a hollow barrel, a plunger end and a needle end, a piston mounted within the barrel, a needle assembly including a hub and a needle, said hub having a front shoulder, a radially extending rear shoulder, and the needle assembly mounted to the needle end;
 a hollow enclosure unit sized for housing the cartridge-needle unit therein, the enclosure unit comprising:
  a body section for housing the barrel, the body section having a plunger end and a needle end having an opening so that the needle may pass therethrough, the needle end also having a necked down portion sized smaller than the hub so that the hub cannot pass through the opening;
  a stem engageable with the piston to enable a user to drive the piston along the barrel from the plunger end of the barrel assembly;
  and means for engaging said hub in said body section, thereby securing said needle assembly in the body section with the needle fully within the body section, and preventing further movement of the cartridge-needle unit from a safe position, the means for engaging said hub in the body section including at least one protrusion that is inwardly biasable and extending outwardly from said body section in a natural, unbiased position, and a sleeve sized to fit around the outer surface of said body section, wherein said protrusion is biased inwards towards the central axis of the body section when exposed to a biasing force exerted by said sleeve when said sleeve is positioned around said body section, whereby the inner wall of said sleeve engages the protrusion to bias the protrusion inwardly toward the central axis of the body section until the protrusion engages the hub to secure said hub in a stationary position within the body section and prevent removal of the needle assembly from said body section when the cartridge-needle unit is positioned in the body section having the needle portion fully contained within.

3. The syringe of claim 2 further comprising a catch pin integral with and extending from the body section into a hollow channel, said hollow channel located in the body section, such that when the sleeve passes over said catch pin, the catch pin biases inward allowing the sleeve to pass over it, said sleeve further comprising a catch pin aperture which, when positioned over the catch pin, allows the catch pin to return to its natural, unbiased position, said catch pin aperture engaging the catch pin and locking the sleeve into the body section.

4. The syringe of claim 2 wherein the protrusion includes a raised detent integral with and extending from said body section into a hollow channel such that the detent biases inwardly when the sleeve passes over it.

5. The syringe of claim 2 wherein the plunger end of the body section includes assembly ramps configured to allow the sleeve to pass onto the outer surface of the body section when the sleeve and the body section are forced toward one another along the central axis of the body section.

6. The unit of claim 2 wherein a portion of the plunger end of the body section is configured to prevent the barrel hub of the cartridge-needle unit from passing through the plunger end of the body section.

7. The unit of claim 6 wherein the body and stem sections of the enclosure unit are molded as a single piece and the stem section is frangibly connected to the body section.

8. The unit of claim 7 wherein the body section has a constant diameter over at least one-third of its length as measured from its needle end.

9. The unit of claim 8 wherein said sleeve further comprises an end portion frangibly connected at the plunger end to permit the cartridge-needle unit to be at least partially withdrawn from said remainder of the body section through the plunger end so to position the needle assembly at a safe position with the needle entirely within the body section.

10. A unitary molded set of the enclosure units of claims 2, 3, 4, 5, 6, 7, 8 or 9 including frangible connections coupling adjacent ones of said enclosure units to one another.

11. The disposable safety syringe of claim 2 further comprising a plurality of stabilizing tabs in hinged connection to said body section having a unlocked position and a locked position, means for securing said stabilizing tabs in said locked position, wherein in said locked position said stabilizing tabs centrally position said cartridge-needle unit in said body section.

12. The syringe of claim 2 wherein the sleeve further comprises a removable end portion removably attached to the plunger end of the body section.

13. The syringe of claim 12 wherein the removable end portion includes a hinged cap.

* * * * *